(12) United States Patent
Fujita

(10) Patent No.: US 6,449,040 B1
(45) Date of Patent: Sep. 10, 2002

(54) SPECTROPHOTOMETER WITH VALIDATION PROGRAMS

(75) Inventor: Takeshi Fujita, Kyoto (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 09/438,593

(22) Filed: Nov. 12, 1999

(30) Foreign Application Priority Data

Nov. 11, 1998 (JP) .......................................... 10-320268

(51) Int. Cl.[7] .................................................. G01J 3/02
(52) U.S. Cl. ........................ 356/319; 356/246; 356/326
(58) Field of Search ................................ 356/319, 323, 356/325, 326, 328, 244, 246

(56) References Cited

U.S. PATENT DOCUMENTS 4,645,343 A * 2/1987 Stockdale et al. .......... 356/326
5,557,544 A * 9/1996 Simon et al. ............... 356/246
5,638,171 A * 6/1997 Honig et al. ............... 356/246
5,892,458 A * 4/1999 Anderer et al. .......... 340/10.41

* cited by examiner

Primary Examiner—F L Evans
(74) Attorney, Agent, or Firm—Beyer Weaver & Thomas LLP

(57) ABSTRACT

A spectrophotometer has not only an optical system for irradiating a cell with light having a specified wavelength, a detector for detecting light received from the cell and a data processor for precessing data based of detection signals from the detector, but also a cell sensor and a cell identifier for detecting whether a cell is mounted and, if so, the kind of the mounted cell, a program memory which stores validation programs for carrying out validation tests and a validation controller for retrieving from the program memory one of the stored validation programs corresponding to the identified kind of the cell and carrying out the retrieved validation program.

8 Claims, 2 Drawing Sheets

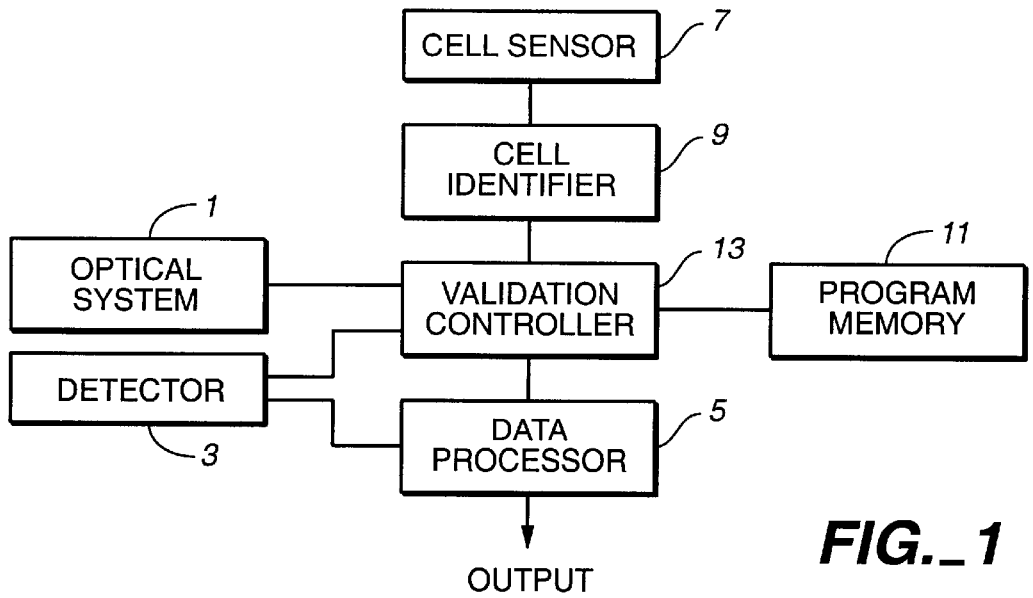
FIG._1
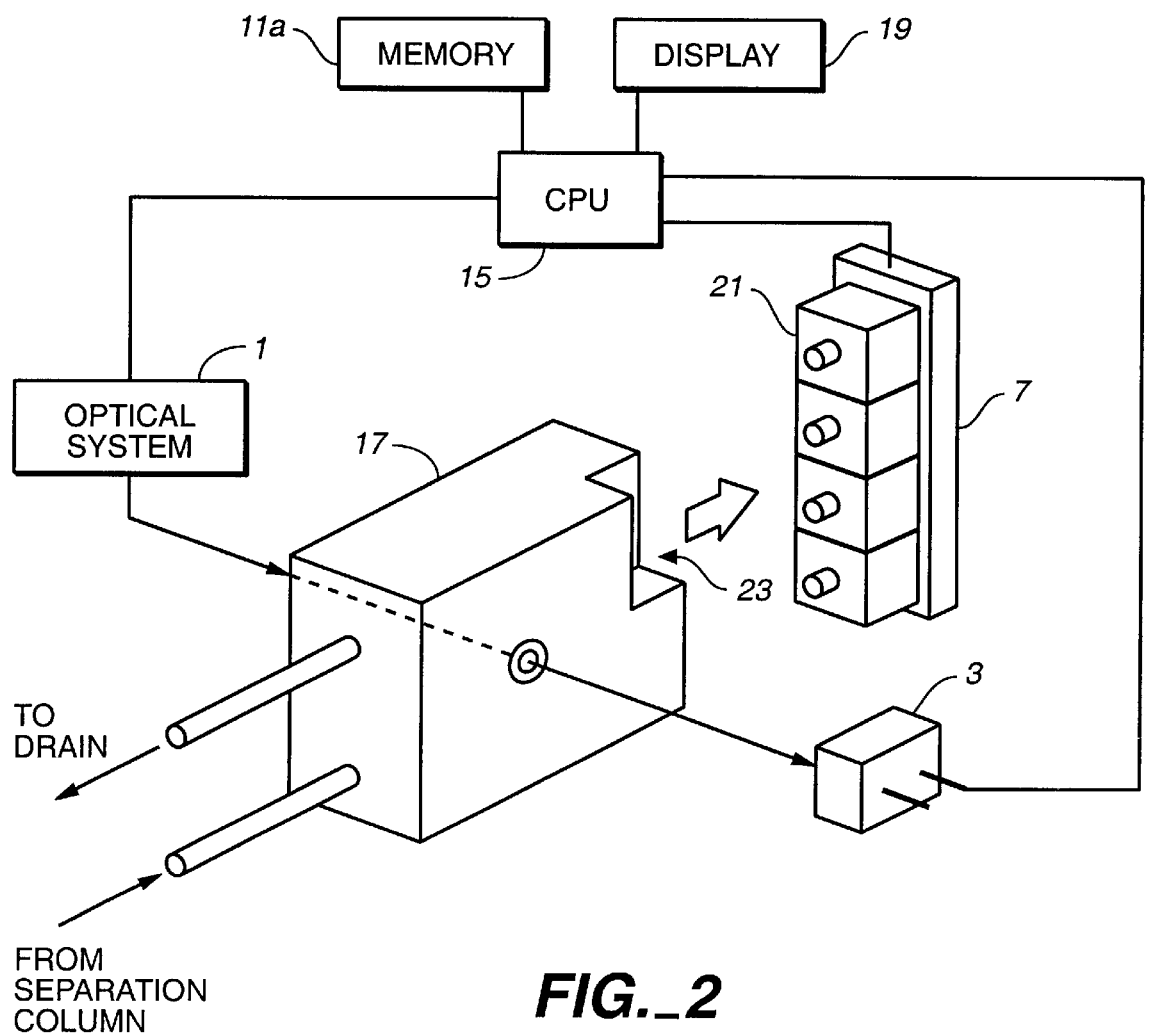
FIG._2

SPECTROPHOTOMETER WITH VALIDATION PROGRAMS

BACKGROUND OF THE INVENTION

This invention relates to a spectrophotometer for detecting components of a sample inside a cell by exposing it to light, and more particularly to such a spectrophotometer having validation programs therefor stored in a memory corresponding to the kind of cell used for the testing. Such a spectrophotometer may be used either singly or as a detector, for example, for a liquid chromatograph.

When a spectrophotometer is used as a detector for a liquid chromatograph, its cell is irradiated with light as a sample separated in the column passes through it together with a solvent, and the concentrations of its components are quantitatively analyzed by measuring the absorptivity and the coefficient of refraction of this light. Many different kinds of cells are available such as standard cells, microcells with a small inner diameter, high-pressure cells with a high resistance against high pressures and fractioning cells having a shorter optical path, which may be used selectively, depending on the purpose and/or conditions of the analysis.

Prior to an analysis, the spectrophotometer is sometimes made to undergo so-called validation tests, say, for a measurement of drift noise, a wavelength correction and a determination of accuracy in light measurements. In such a case, the user is usually required to select software and hardware from a menu. This has been a cumbersome procedure.

SUMMARY OF THE INVENTION

It is therefore an object of this invention to provide an improved spectrophotometer on which various validation processes can be carried out without any cumbersome procedure.

A spectrophotometer embodying this invention, with which the above and other objects can be accomplished, may be characterized as comprising not only an optical system for irradiating a cell with an incident beam of light having a specified wavelength, a detector for detecting light received from the cell and a data processor for precessing data based on detection signals from the detector, but also a cell sensor and a cell identifier for detecting whether a cell is mounted and, if so, the kind of the mounted cell, a program memory which stores validation programs for carrying out validation tests and a validation controller for retrieving from the program memory one of the stored validation programs corresponding to the identified kind of the cell and carrying out the retrieved validation program. It is thus adapted to have any of a plurality of validation cells mounted thereto and to automatically start a validation process associated with the kind of the validation cell which is mounted.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a block diagram of a spectrophotometer embodying this invention;

FIG. 2 is a sketch, including a block diagram, of a portion of a liquid chromatograph incorporating a spectrophotometer such as shown in FIG. 1.

Throughout herein, components which are mutually equivalent are indicated by the same numerals and are not necessarily described repetitiously for the convenience of the disclosure.

DETAILED DESCRIPTION OF THE INVENTION

Figure 3:
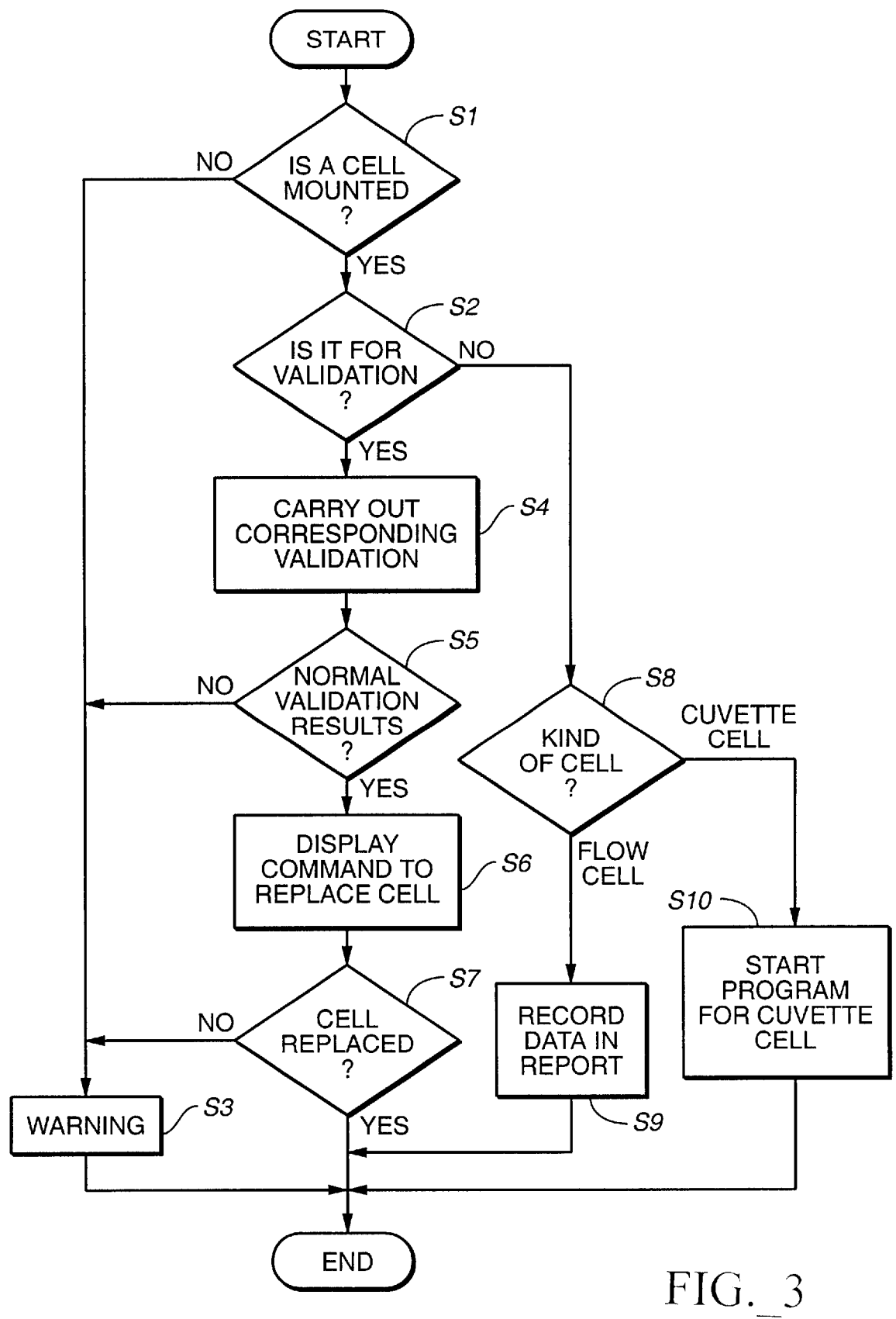
FIG. 3 is a flow chart of the operation for identifying cells by the spectrophotometer of FIG. 2.

The invention is described next by way of an example. FIG. 1 shows the structure of a spectrophotometer embodying this invention, comprising an optical system 1 for irradiating a cell (say, for a liquid chromatograph) with light having a specified wavelength, a detector 3 for detecting light from the cell and a data processor 5 for processing data based on detection signals outputted from the detector 3. The spectrophotometer is provided also with a cell sensor 7 for detecting the kind of the cell which is mounted and outputting cell information based on the kind of the cell as determined thereby, a cell identifier 9 which identifies the kind of the cell based on the cell information outputted from the cell sensor 7, a program memory 11 which stores routine programs for carrying out validation test processes, and a validation controller 13 which serves to retrieve from the program memory 11 a routine program corresponding to cell information received from the cell identifier 9 when a cell for carrying out validation has been detected by the cell identifier 9 and to thereby control the optical system 1, the detector 3 and the data processor 5 to carry out the validation test process.

Not all cells that may be mounted are for validation. If the cell identifier 9 determines by analyzing the cell information received from the cell sensor 7 that the cell which is mounted is a cell for carrying out validation, the received cell information is transmitted to the validation controller 13, causing the validation controller 13 thereupon not only to retrieve from the program memory 11 a routine program corresponding to the transmitted cell information but also to control the optical system 1 and the detector 3 accordingly to carry out the corresponding validation test.

FIG. 2 shows an ultraviolet-visible light spectrophotometer of the present invention used as a detector for a liquid chromatograph. A light beam from an optical system 1 including a lamp is introduced to a flow cell 17 of which the inlet to its flow route is connected to the separation column (not shown) of the liquid chromatograph and the outlet is connected to a drain. The transmitted light from the flow cell 17 is detected by a photosensor 3 serving as a detector. The photosensor 3 outputs a detection signal in response, and this detection signal is received by and processed by a central processing unit (CPU) 15.

At the position where the cell 17 is mounted is a microsensor array 7 (serving as a mechanical cell sensor of a contact type) for identifying not only whether a cell is mounted or not but also the kind of the cell if it is mounted. Four switches 21 each with a push button are provided to the microsensor array 7. Each of these switches is connected to the CPU 15 and is normally in the OFF condition, being switch to the ON condition when the corresponding button is pushed in.

A notch 23 may or may not be formed at each of the positions corresponding to the switches 21 on the surface of the cell 17 where the microsensor array 7 is contacted. When the cell 17 is mounted, those of the switches 21 corresponding to a notch will remain in the OFF condition but those at a position where there is no notch will have their buttons pushed in and become switched to the ON condition. Thus, by varying the number and positions of the notches formed on the cell 17, $2^4-1=17$ different kinds of cells can be identified, the cell identifier 9 concluding that there is no cell mounted if all four switches 21 are in the OFF condition.

The CPU 15, which plays the role of both the validation controller 13 and the data processor 5 described above with reference to FIG. 1, also controls the operations of the optical system 1. A memory device 11a which includes the program memory 11 and a display device 19 are connected to the CPU 15.

The process of identifying cells is explained next with reference to the flow chart of FIG. 3.

When the cell 17 is mounted (YES in Step S1), the microsensor array 7 transmits the corresponding cell information to the cell identifier 9 and its kind is thereby identified (Step S2). A warning is displayed (Step S3) if the cell 17 is not mounted (NO in Step S1). If the cell identifier 9 identifies the mounted cell 17 to be one of validation cells (YES in Step 2) on the basis of the received cell information, the cell information is further transmitted from the cell identifier 9 to the validation controller 13. When this information is received, the validation controller 13 retrieves a validation program for the measurement of drift noise, correction of wavelength or the determination of accuracy in light measurement according to the received cell information and automatically carries out the process of validation by controlling the optical system 1, the detector 3 and the data processor 5 (Step S4). If an abnormal result is obtained by the validation (NO in Step S5), a warning is displayed (Step S3). If no abnormality is detected in the validation (YES in Step S5), a command message that the cell for the validation process should now be replaced by another cell which is for carrying out an analysis (Step S6). Until the specified cell is mounted instead (NO in Step S7), a warning keeps appearing on the display device 19 (Step S3).

If the validation cell is replaced by the specified kind of cell for carrying out an analysis and the cell identifier 9 identifies it as such (NO in Step S2), and if it is further determined that it is a flow cell (Step S8) such as a standard cell, a semi-micro cell or a fractioning cell, data on this flow cell such as the length of the optical path are recorded in a recording area (not shown) as well as a report on the result of analysis. If it is identified to be a cuvette cell, the program stored in the memory device 11a for using the system as a spectrophotometer is started (Step S10). After the kind of the cell has thus been identified, the program corresponding to this kind is started.

Thus, the process for validation can be automatically started by merely mounting a cell therefor. Moreover, when a validation program is carried out for checking a linearity characteristic by using cells for determining accuracy in light measurement, several (say, 4 to 5) cells containing a standard liquid at different concentrations are sequentially mounted. Errors which may be made in such a routine by the mounting of the cells in a wrong sequence can be prevented according to this invention because each of these cells can be automatically identified by the positions of the notches formed on the individual cells.

The examples described above are not intended to limit the scope of the invention. Many modifications and variations are possible within the scope of the invention. For example, there is no need to use mechanical contact type switches as the cell identifier. Other kinds of identifier such as photo-interrupters of light transmitting or reflecting type or a Hall element can be used for the same purpose. Since there are situations in which parameters for the analysis such as the pump flow rate must be changed, depending on the kind of the cell, for example, when a fractioning cell or a high-pressure cell is used, the control program may be so modified that such parameters for the analysis are also so changed, depending on the kind of cell information received from the cell identifier. Moreover, the present invention is not limited to applications to ultraviolet and visible light spectrophotometers for a liquid chromatograph but may be applied to all kinds of spectrophotometers including fluorescence detectors.

What is claimed is:

1. A spectrophotometer comprising:

an optical system for irradiating a cell with light of a specified wavelength;

a detector for detecting light received from said cell;

a data processor for precessing data based on detection signals received from said detector;

a cell sensor for sensing said cell and outputting cell information indicating a kind of said sensed cell;

a cell identifier for identifying the kind of said sensed cell according to said cell information;

a program memory storing validation programs for carrying out validation of said spectrophotometer; and a validation controller for retrieving from said program memory one of said validation programs corresponding to said cell information and carrying out said retrieved validation program by controlling said optical system, said detector and said data processor.

2. The spectrophotometer of claim 1 wherein said identifier outputs said cell information to said validation controller.

3. The spectrophotometer of claim 1 wherein said cell sensor detects the kind of said cell by contacting said cell.

4. The spectrophotometer of claim 1 wherein said cell is one of a plurality cells of different kinds including cells which are not for validation.

5. The spectrophotometer of claim 4 wherein said cell sensor comprises a plurality of switches each having a push button, push buttons of a different combination of said switches being pushed in when a different one of said plurality of cells is mounted to said spectrophotometer and detected by said cell sensor.

6. The spectrophotometer of claim 1 wherein said cell identifier, said validation controller and said data processors are realized by a central processing unit.

7. The spectrophotometer of claim 6 further comprising a display device, said central processing unit serving to cause a warning displayed on said display device if said retrieved validation program yields an abnormal result.

8. The spectrophotometer of claim 6 further comprising a display device, said central processing unit serving to display on said display device a command that a cell of a specified kind be mounted and to cause a warning displayed on said display device until a cell of said specified kind is detected by said cell sensor.

* * * * *